April 29, 1958 E. S. BOERNER Plant Pat. 1,697
CHRYSANTHEMUM PLANT
Filed Sept. 9, 1957
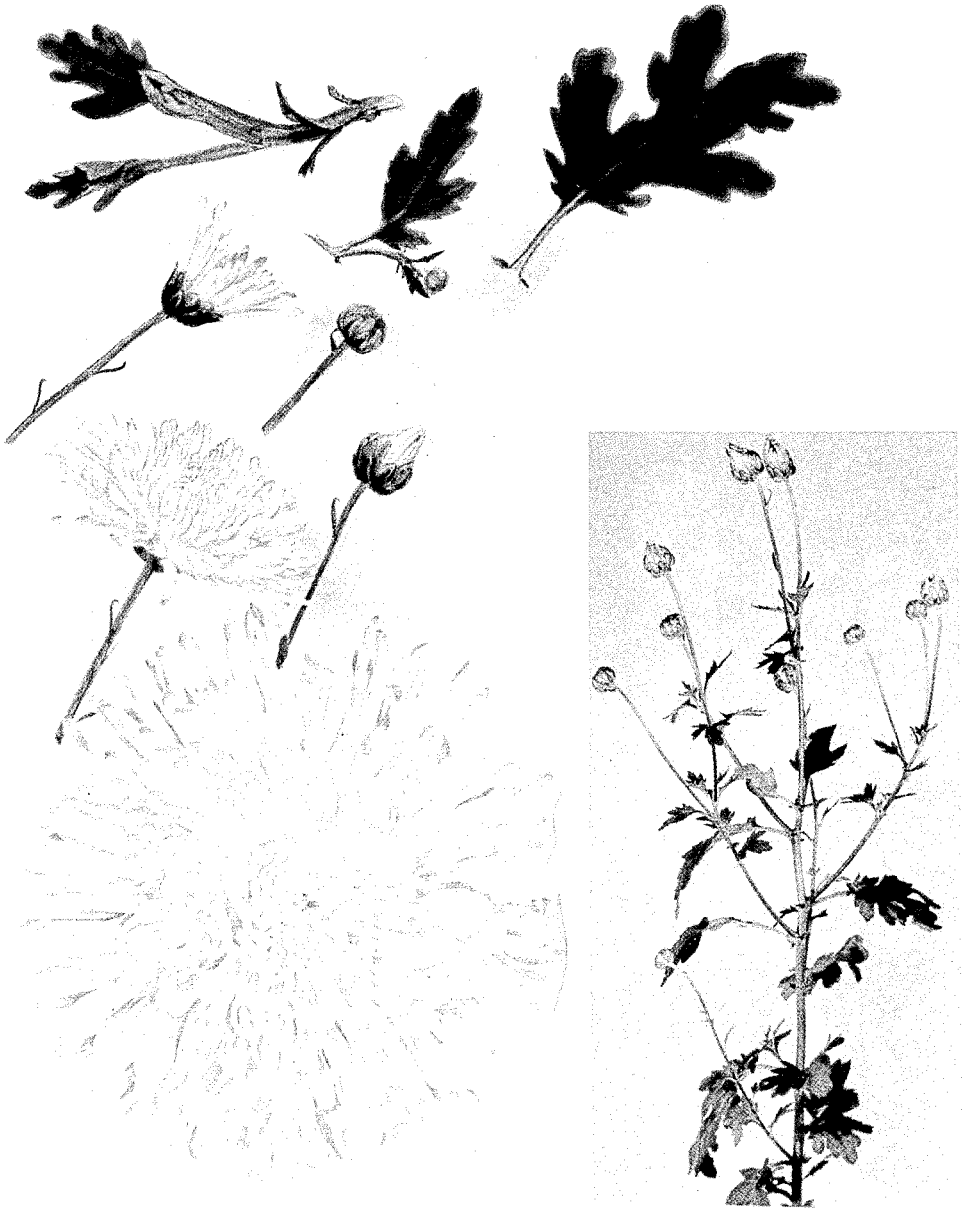
Inventor.
E. S. Boerner
By: Robbins Robb
Attorneys.

United States Patent Office

Plant Pat. 1,697
Patented Apr. 29, 1958

1,697

CHRYSANTHEMUM PLANT

Eugene S. Boerner, Newark, N. Y., assignor to Jackson & Perkins Company, Newark, N. Y., a corporation of New York Application September 9, 1957, Serial No. 682,989

1 Claim. (Cl. 47—60)

The present invention relates to a new and distinct variety of chrysanthemum plant of the semi-spoon type, which was originated by me by crossing the variety "Flicker" (Plant Patent No. 1,465) with the variety "Canary" (Plant Patent No. 1,113).

The primary objective of this breeding was to produce a new chrysanthemum variety characterized by the floriferousness of the parent variety "Canary," and by the strength of the parent variety "Flicker." This objective was fully achieved, along with other improved features, as evidenced by the following characteristics which are outstanding in the new variety and which represent a unique combination in a chrysanthemum of this class:

(1) A floriferous habit;
(2) Strong flower stems;
(3) Large flowers;
(4) Very double flower form;
(5) Semi-spoon form of the flower petals; and
(6) A distinctive Mikado Orange general color tonality of the flowers, with their outer edges lightly overcast with Light Orange-Yellow.

The foregoing characteristics and distinctions definitely differentiate the new variety from its parents, as well as from all other varieties of its class of which I am aware, and asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black-and-white, as illustrative of the form and habit of growth of the plant.

The following is a detailed description of my new variety, with color terminology in accordance with Ridgway's Color Standards and Nomenclature, as based upon observations made from specimens grown outdoors at Newark, New York, in the early morning in the latter part of the month of September:

Parentage: "Flicker" × "Canary."
Classification: Semi-spoon.

Growth: Clean; upright; attains a height averaging about 30 inches.
Cold resistance: The plant is very winter hardy in northern New York, and the flowers are frost-resistant.
Blooming period: In the Newark, New York climatic area, blooming begins about September 20th and continues until frosts.

*Flower*

Bud:
*Color.*—When sepals first divide—Light Ochraceous Buff, Plate 15. When petals begin to unfurl—Light Orange-Yellow, Plate 3, lightly overcast with Grenadine Pink, Plate 2 on outer edge of petal. When half-blown: inside of petals—Orange-Buff, Plate 3, with lower half of petal lightly overcast with Light Orange-Yellow, Plate 3; reverse of petals—Salmon-Orange, Plate 2, with lower half of petal lightly overcast with Light Orange-Yellow, Plate 3.
*Peduncle.*—Strong; erect. Color—Chromium Green Plate 32.

Bloom:
*Size.*—5½ inches.
*Stems.*—Strong; normal.
*Form.*—Semi-spoon.
*Petalage.*—Very double.
*Color.*—Center of flower—Deep Chrome, Plate 3. Outer petals—Light Orange-Yellow, Plate 3, lightly overcast with Mikado Orange, Plate 3 in the center of the petal. Base of petals—Picric Yellow, Plate 4. Inside of petals—Mikado Orange, Plate 3, with outer edges lightly overcast with Light Orange-Yellow, Plate 3. Reverse of petals—Ivory Yellow, Plate 30, lightly overcast with Pale Ochraceous Salmon, Plate 15.
*Petals.*—Texture—stiff; waxy. Form—semi-spoon, with lower half of petal quilled.
*Fragrance.*—Characteristic chrysanthemum.

*Plant*

Form: Upright.
Growth: Bushy; vigorous.
Foliage:
*Size.*—Medium.
*Quantity.*—Normal.
*Color.*—Upper side—Varley's Green, Plate 18. Under side—Light Cress Green, Plate 31.
*Texture.*—Leathery.

I claim:

A new and distinct variety of chrysanthemum plant of the semi-spoon type, substantially as herein shown and described, characterized particularly as to novelty by its floriferous habit, its strong flower stems, the large size of its flowers, the very double form of the flowers, the semi-spoon form of the flower petals, and the distinctive Mikado Orange general color tonality of its flowers with their outer edges lightly overcast with Light Orange-Yellow.

No references cited.